US009458210B2

(12) United States Patent
Ikezono et al.

(10) Patent No.: US 9,458,210 B2
(45) Date of Patent: Oct. 4, 2016

(54) ANTIBODY REACTING WITH NATIVE COCHLIN-TOMOPROTEIN (CTP) AND METHOD FOR MEASURING CTP USING SAME

(75) Inventors: Tetsuo Ikezono, Iruma-gun (JP); Satomi Shikaze, Tokyo (JP)

(73) Assignee: SAITAMA MEDICAL UNIVERSITY, Saitama (JP)

( * ) Notice: Subject to any disclaimer, the term of this patent is extended or adjusted under 35 U.S.C. 154(b) by 424 days.

(21) Appl. No.: 14/008,677

(22) PCT Filed: Apr. 2, 2012

(86) PCT No.: PCT/JP2012/058988
§ 371 (c)(1),
(2), (4) Date: Sep. 30, 2013

(87) PCT Pub. No.: WO2012/133898
PCT Pub. Date: Oct. 4, 2012

(65) Prior Publication Data
US 2014/0030742 A1 Jan. 30, 2014

(30) Foreign Application Priority Data
Mar. 31, 2011 (JP) ................................. 2011-080052

(51) Int. Cl.
*C07K 14/47* (2006.01)
*C07K 16/18* (2006.01)
*G01N 33/68* (2006.01)

(52) U.S. Cl.
CPC ............... *C07K 14/47* (2013.01); *C07K 16/18* (2013.01); *G01N 33/6893* (2013.01); *C07K 2317/33* (2013.01); *C07K 2317/34* (2013.01); *G01N 2800/14* (2013.01)

(58) Field of Classification Search
CPC .. C07K 14/47; C07K 16/18; C07K 2317/34; C07K 2317/33; G01N 33/6893; G01N 2800/14
See application file for complete search history.

(56) References Cited

U.S. PATENT DOCUMENTS

| 6,228,600 B1* | 5/2001 | Matsui | C07K 14/71 435/21 |
| 2002/0086988 A1* | 7/2002 | Conklin | C07K 14/47 536/23.5 |
| 2006/0246516 A1 | 11/2006 | Ikezono et al. | |
| 2008/0227113 A1* | 9/2008 | Pentyala | C07K 16/40 435/7.1 |
| 2009/0075306 A1 | 3/2009 | Tuohy et al. | |

FOREIGN PATENT DOCUMENTS

JP 2004-85552 3/2004

OTHER PUBLICATIONS

International Search Report issued May 15, 2012 in International (PCT) Application No. PCT/JP2012/058988, (two pages).
Ikezono et al., "Cochlin-Tomoprotein: A Novel Perilymph-Specific Protein and a Potential Marker for the Diagnosis of Perilymphatic Fistula", Audiology & Neurotology, vol. 14, 2009, pp. 338-344.
Ikezono et al., "The Performance of Cochlin-Tomoprotein Detection Test in the Diagnosis of Perilymphatic Fistula", Audiology & Neurotology, vol. 15, 2010, pp. 168-174.
Ikezono et al., "CTP (Cochlin-tomoprotein) detection in the profuse fluid leakage (gusher) from cochleostomy", Acta Oto-Laryngologica, vol. 130, 2010, pp. 881-887.
Li et al., "Molecular cloning of the Coch gene of guinea pig inner ear and its expression analysis in cultured fibrocytes of the spiral ligament", Acta Oto-Laryngologica, vol. 130, 2010, pp. 868-880.
Ikezono et al., "Identification of a novel Cochlin isoform in the perilymph: insights to Cochlin function and the pathogenesis of DFNA9", Biochemical and Biophysical Research Communications, vol. 314, 2004, pp. 440-446.
Ikezono, T., "Cochlin-Tomoprotein (CPT) as a diagnostic marker for perilymph fistula", Rinsho Kensa, vol. 49, No. 11, 2005, pp. 1259-1263, with English translation and the specification.
English Translation of International Preliminary Report on Patentability issued Oct. 17, 2013 in International Application No. PCT/JP2012/058988.

* cited by examiner

Primary Examiner — Christine Foster
(74) Attorney, Agent, or Firm — Wenderoth, Lind & Ponack, L.L.P.

(57) ABSTRACT

An immunological measurement is performed using anti-CTP antibody characterized by recognizing an antigenic determinant included in the polypeptide represented by amino acid numbers 118-132 of SEQ ID NO: 1, and reacting with native Cochlin-tomoprotein (CTP).

13 Claims, 1 Drawing Sheet

Fig. 1

```
0    12345678901234567890123456789012345678901234567890
     MSAAVIPALGLGVLLLLPGPAGSEGAAPIAITCFTRGLDIRKEKADVLC
          Signal peptide              TRGLDIRKEKADVLC      LCCL; 36-50
                                     CFTRGLDIRKEKADVL      CTP-A; 34-49

50   12345678901234567890123456789012345678901234567890
     PGGCPLEEFSVYGNIVYASVSSICGAAVHRGVISNSGGPVRVYSLPGREN
          LCCL1; 63-83  GNIVYASVSSICGAAVHRGVI
                                       LCCL2; 95-111   LPGREN
                           CTP-B; 91-108   C+RVYSLPGREN 100  1234567890123456789012345678901 2
     YSSVDANGIQSQMLSRWSASFTVTKGKSSTQE
     YSSVDANGIQS+C
      YSSVDANG
                   LSRWSASFTVTKGK+C    LCCL3; 114-127
                      C+SASFTVTKGKSSTQE   CTP-C; 118-132
```

Fig. 2

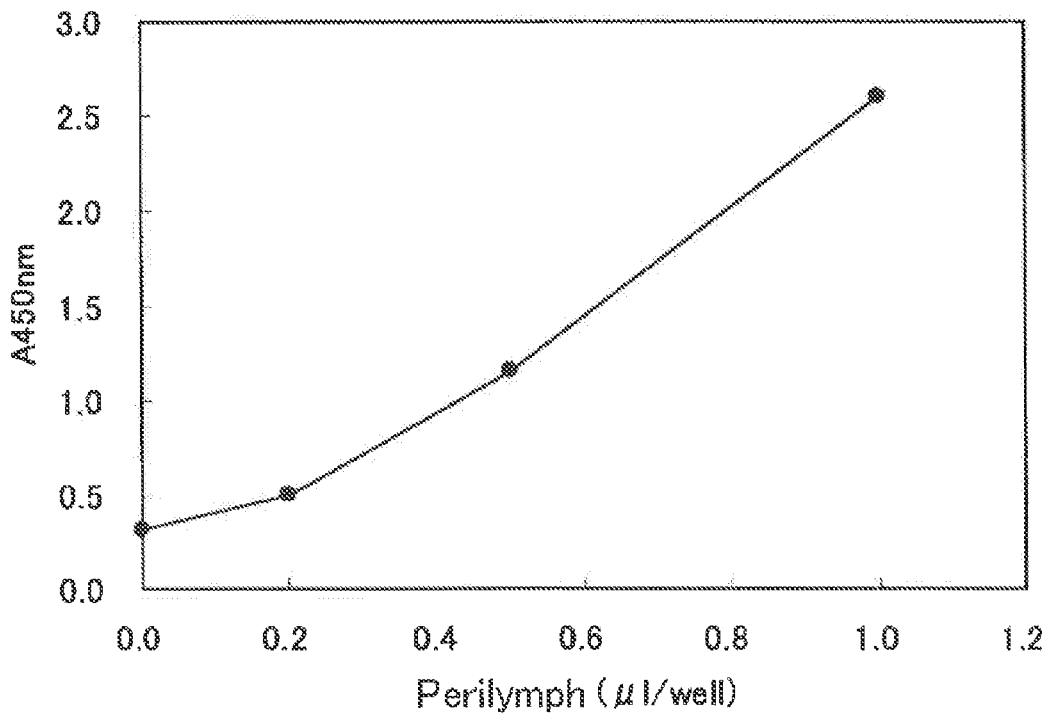

SEQUENCE LISTING

```
<160> NUMBER OF SEQ ID NOS: 10

<210> SEQ ID NO 1
<211> LENGTH: 132
<212> TYPE: PRT
<213> ORGANISM: Homo sapiens

<400> SEQUENCE: 1

Met Ser Ala Ala Trp Ile Pro Ala Leu Gly Leu Gly Val Cys Leu Leu
1               5                   10                  15

Leu Leu Pro Gly Pro Ala Gly Ser Glu Gly Ala Ala Pro Ile Ala Ile
                20                  25                  30

Thr Cys Phe Thr Arg Gly Leu Asp Ile Arg Lys Glu Lys Ala Asp Val
            35                  40                  45

Leu Cys Pro Gly Gly Cys Pro Leu Glu Glu Phe Ser Val Tyr Gly Asn
        50                  55                  60

Ile Val Tyr Ala Ser Val Ser Ser Ile Cys Gly Ala Ala Val His Arg
65                  70                  75                  80

Gly Val Ile Ser Asn Ser Gly Gly Pro Val Arg Val Tyr Ser Leu Pro
                85                  90                  95

Gly Arg Glu Asn Tyr Ser Ser Val Asp Ala Asn Gly Ile Gln Ser Gln
            100                 105                 110

Met Leu Ser Arg Trp Ser Ala Ser Phe Thr Val Thr Lys Gly Lys Ser
        115                 120                 125

Ser Thr Gln Glu
    130

<210> SEQ ID NO 2
<211> LENGTH: 15
<212> TYPE: PRT
<213> ORGANISM: Homo sapiens

<400> SEQUENCE: 2

Thr Arg Gly Leu Asp Ile Arg Lys Glu Lys Ala Asp Val Leu Cys
1               5                   10                  15
```

<210> SEQ ID NO 3
<211> LENGTH: 21
<212> TYPE: PRT
<213> ORGANISM: Homo sapiens

<400> SEQUENCE: 3

Gly Asn Ile Val Tyr Ala Ser Val Ser Ser Ile Cys Gly Ala Ala Val
1               5                   10                  15

His Arg Gly Val Ile
            20

<210> SEQ ID NO 4
<211> LENGTH: 18
<212> TYPE: PRT
<213> ORGANISM: Homo sapiens

<400> SEQUENCE: 4

Leu Pro Gly Arg Glu Asn Tyr Ser Ser Val Asp Ala Asn Gly Ile Gln
1               5                   10                  15

Ser Cys

<210> SEQ ID NO 5
<211> LENGTH: 15
<212> TYPE: PRT
<213> ORGANISM: Homo sapiens

<400> SEQUENCE: 5

Leu Ser Arg Trp Ser Ala Ser Phe Thr Val Thr Lys Gly Lys Cys
1               5                   10                  15

<210> SEQ ID NO 6
<211> LENGTH: 16
<212> TYPE: PRT
<213> ORGANISM: Homo sapiens

<400> SEQUENCE: 6

Cys Phe Thr Arg Gly Leu Asp Ile Arg Lys Glu Lys Ala Asp Val Leu
1               5                   10                  15

<210> SEQ ID NO 7
<211> LENGTH: 19
<212> TYPE: PRT
<213> ORGANISM: Homo sapiens

<400> SEQUENCE: 7

Cys Arg Val Tyr Ser Leu Pro Gly Arg Glu Asn Tyr Ser Ser Val Asp
1               5                   10                  15

Ala Asn Gly

<210> SEQ ID NO 8
<211> LENGTH: 16
<212> TYPE: PRT
<213> ORGANISM: Homo sapiens

<400> SEQUENCE: 8

Cys Ser Ala Ser Phe Thr Val Thr Lys Gly Lys Ser Ser Thr Gln Glu
1               5                   10                  15

<210> SEQ ID NO 9
<211> LENGTH: 20
<212> TYPE: DNA
<213> ORGANISM: Artificial Sequence
<220> FEATURE:

```
<223> OTHER INFORMATION: primer

<400> SEQUENCE: 9
atgatcacat gttttaccag                                              20

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
tattcattac tcctgtgtac tact                                         24
```

US 9,458,210 B2

ANTIBODY REACTING WITH NATIVE COCHLIN-TOMOPROTEIN (CTP) AND METHOD FOR MEASURING CTP USING SAME

TECHNICAL FIELD

The present invention relates to an antibody reacting with native CTP, a kit comprising the antibody and an immunological measuring method using the antibody. The present invention further relates to a method of screening for an antibody reacting with native CTP.

BACKGROUND ART

Cochlin-tomoprotein (hereinafter referred to as CTP), which is a 16 kDa isoform of Cochlin present in perilymph, is a promising diagnostic marker for perilymph fistula because it is not found in other body fluids which can be present in the middle ear such as cerebrospinal fluid, blood and saliva (Patent Literature 1, Nonpatent Literatures 1-5). Perilymph fistula is a disease in which inner ear dysfunction is manifested when labyrinthine window separating the inner ear from the middle ear is ruptured, and then perilymph with which the inner ear is filled leaks into the middle ear. Because the symptom may be ameliorated by closing labyrinthine window in the early stage of the onset, early diagnosis is very important.

So far, the research group of the present inventors has produced four rabbit polyclonal antibodies using a synthetic peptide as an immunogen in order to measure CTP in a biological sample (Patent Literature 1). However, all of the antibodies only react with denatured CTP. An antibody reacting with native CTP has not been obtained. In Nonpatent Literatures 1-5, therefore, the above anti-LCCL3 antibody which recognizes denatured CTP (which does not react with native CTP) is used to measure CTP in a biological sample by Western blotting.

CITATION LIST

Patent Literature

Patent Literature 1: Japanese Patent Laid-Open No. 2004-85552

Nonpatent Literature

Nonpatent Literature 1: Ikezono et al. *Biochem Biophys Res Commun.* 2004; 314: 440-446
Nonpatent Literature 2: Ikezono et al., *Audiol Neurotol* 2009; 14: 338-344
Nonpatent Literature 3: Ikezono et al., *Audiol Neurotol* 2010; 15: 168-174
Nonpatent Literature 4: Ikezono et al., *Acta Oto-Laryngologica* 2010; 130; 881-887
Nonpatent Literature 5: Tetsuo Ikezono, *Rinsho Kensa*, vol. 49, no. 11 (December, 2005): p 1259-1263 (2005)

SUMMARY OF INVENTION

However, measurements under denatured conditions, in which CTP in a biological sample cannot be measured in its native state, may result in false negative and false positive, and may be susceptible to contaminating proteins. The measurements also require complicated procedures and are time-consuming before obtaining results. Therefore, a method of measuring CTP in a faster, simpler and more accurate fashion is demanded.

In order to measure CTP in a biological sample more simply and accurately, the research group of the present inventors has tried to raise a monoclonal antibody using recombinant CTP expressed in *E. coli* as an immunogen in addition to the 4 polyclonal antibodies described in Patent Literature 1. Nonetheless, a high antibody titer was difficult to be achieved, and only few clones were obtained, because CTP is present in a wide variety of animal species such as mouse, swine and bovine, and its homology is high between animal species. The clones obtained were reactive only in denatured conditions. An antibody reacting with native CTP was not obtained.

Because only a trace amount of CTP is present in a living organism, it is not possible to prepare CTP from a biological sample in an amount enough to use it as an immunogen for raising an antibody. Therefore, it is necessary to raise an antibody by using a synthetic peptide, a recombinant protein and the like as an immunogen. However, as mentioned above, neither the antibody against a synthetic peptide nor the antibody against recombinant CTP expressed in *E. coli* reacted with native CTP. This suggests that CTP forms a highly complex tertiary structure in a biological sample. Usually, a strain having good reactivity with an antigen used for immunization is selected at a screening process in antibody production. In the case of CTP, the three dimensional structure of the recombinant protein used for immunization differs from that of CTP present in a biological sample. Therefore, even if a done recognizing native CTP has been raised, it may not be selected at the screening process due to poor reactivity with the immunogen. As a result, an antibody which recognizes native CTP is much more difficult to be obtained.

Accordingly, in order to solve the problem described above, the present invention provides an antibody which recognizes native CTP. The present invention further provides a method of measuring CTP in a biological sample using the antibody. Moreover, the present invention provides a method of screening for an antibody which recognizes native CTP.

The present inventors found that native CTP can be measured by using an antibody which recognizes an epitope in a peptide sequence of CTP-C (amino acid numbers 118-132 of SEQ ID NO: 1). Further, the present inventors found that an antibody which recognizes native CTP can be obtained by selecting an antibody reacting with native CTP captured by anti CTP-C antibody solid-phased on a support. Then the present inventors completed the present Invention The present invention includes:

(1) An antibody which recognizes an antigenic determinant included in the polypeptide represented by amino acid numbers 118-132 of SEQ ID NO: 1, and reacts with native Cochlin-tomoprotein (CTP).

(2) The anti CTP-antibody according to (1), which is obtainable by using a peptide consisting of amino acid numbers 118-132 of SEQ ID NO: 1 as an immunogen.

(3) A method of screening an antibody reacting with native CTP, comprising providing native CTP captured by a first antibody reacting with native CTP and selecting a second antibody which recognizes the native CTP.

(4) The method of screening an antibody reacting with native CTP according to (3), wherein the first antibody is the antibody according to (1).

(5) An method of immunologically measuring a protein comprising the polypeptide represented by amino acid numbers 118-132 of SEQ ID NO: 1, comprising the step of using at least one antibody according to (1) or (2).

(6) The method according to (5), wherein the protein comprising the polypeptide represented by amino acid numbers 118-132 of SEQ ID NO: 1 is CTP.

(7) A method of examining perilymph fistula, comprising the step of immunologically measuring CTP using at least one antibody according to (1) or (2).

(8) A kit for measuring CTP, comprising at least one antibody according to (1) or (2).

(9) The kit for measuring CTP according to (8), which is used for diagnosing perilymph fistula.

Effects of Invention

The antibody according to the present invention enabled measurement of native CTP. In addition, an antibody which recognizes native CTP can be obtained. This allows perilymph fistula to be diagnosed rapidly and accurately by a simple procedure.

BRIEF DESCRIPTION OF DRAWINGS

FIG. 1 shows the positions of antigenic polypeptides for raising the antibody of the present invention in the amino acid sequence represented by SEQ ID NO: 1. LCCL, shown as TRGLDIRKEKADVLC, is represented by SEQ ID NO:2. CTP-A, shown as CFTRGLDIRKEKADVL, is represented by SEQ ID NO:6. LCCL1, shown as GNIVYASVSSIC-GAAVHRGVI, is represented by SEQ ID NO:3. LCCL2, shown as LPGRENYSSVDANGIQS+C, is represented by SEQ ID NO:4. CTP-B, shown as C+RVYSLPGRENYSS-VDANG, is represented by SEQ ID NO:7. LCCL3, shown as LSRWSASFTVTKGK+C, is represented by SEQ ID NO:5. In addition, CTP-C, shown as C+SASFTVTK-GKSSTQE, is represented by SEQ ID NO:8.

FIG. 2 shows the results from the measurements of serially diluted human perilymph by the sandwich ELISA method using the anti-CTP-C antibody of the present invention and the 3C10 antibody.

DESCRIPTION OF EMBODIMENTS

In the followings, embodiments of the present invention will be described in more detail.

In the present specification, methods of purifying and analyzing proteins and methods of raising an antibody can be performed by or in accordance with the methods described in the standard laboratory manuals such as "Shin Kagakujikken Kouza" (edited by Japanese Biochemical Society; Tokyo Kagaku Dojin Co., Ltd.) and "Antibodies—A Laboratory Manual" (E. Harlow, et al., Cold Spring Harbor Laboratory (1988)) unless otherwise stated.

As used herein, Cochlin is a protein encoded by the gene COCH which is identified as a gene responsible for non-symptomatic hereditary deafness DFNA9 (N. G. Robertson, Nature Genet., 20, 299-303 (1998)). For example, the amino acid sequence of human Cochlin is described in Nature Genet., 20, 299-303 (1998). CTP is an isoform of about 16 kDa which consists of an N-terminal fragment of Cochlin. CTP is found in a wide variety of animal species such as bovine, swine, guinea pig, rat and mouse as well as human, but human CTP is preferred. The amino acid sequence of human CTP is shown in SEQ ID NO: 1. The region represented by amino acid numbers 1-24 in the amino acid sequence is a signal sequence.

1. Antibody Reacting with Native CTP

The antibody of the present invention recognizes an antigenic determinant (hereinafter may be referred to as an "epitope") included in the polypeptide represented by amino acid numbers 118-132 of SEQ ID NO: 1, and reacts with native CTP. Preferably, the antibody does not react with any proteins other than a protein comprising the polypeptide represented by amino acid numbers 118-132 of SEQ ID NO: 1. The antibody of the present invention may further react with denatured CTP as long as it reacts with native CTP. In addition, the antibody of the present invention may react with an isoform of Cochlin comprising the polypeptide represented by amino acid numbers 118-132 of SEQ ID NO: 1. In this context, another isoform of Cochlin comprising the polypeptide represented by amino acid numbers 118-132 of SEQ ID NO: 1, p63, is known in addition to CTP (Ikezono et al., Biochem. Biophys. Acta, 1535, 3, 258-265 (2001)). The antibody of the present invention may react with p63.

Native CTP refers to a CTP which is not subjected to a denaturing treatment where the tertiary structure of the protein is significantly altered. Denaturing treatments include, for example, addition of protein denaturing agents (surfactants such as SDS; reducing agents such as DTT; urea; acetone; and the like) and a heat treatment. It should be noted that a low concentration of surfactant and the like may be contained in a sample diluent for immunoassay, and such conditions are not considered to be a denaturing treatment.

Anti CTP antibody can be raised using, for example, a polypeptide consisting of amino acid numbers 118-132 of SEQ ID NO: 1 (hereinafter may be referred to as an "antigen polypeptide") as an immunogen. An antigen polypeptide may be a synthetic polypeptide chemically synthesized in accordance with a known method, or may be a polypeptide produced by the recombinant DNA technique and the like.

An antibody can be raised by using a publicly known and commonly used method. The antibody of the present invention may be polyclonal or monoclonal antibody. Specifically, in a case where polyclonal antibody is raised, the above antigen polypeptide is attached to a carrier protein such as (keyhole limpet hemocyanin), BSA (bovine serum albumin) and swine thyroid globulin using a suitable condensing agent such as carbodiimide and maleimide to prepare an antigen for immunization (an immunogen). An antigenic polypeptide can be attached to a carrier protein by a publicly known method. For example, in a case where the antigenic polypeptide is attached via maleimidization using KLH as a carrier protein, KLH is reacted with a bifunctional condensing agent such as Sulfo-SMCC (Sulfosuccimidyl 4-(N-maleimidomethyl)cyclohexane-1-carboxylate) for maleimidization, and then reacted with the antigenic polypeptide in which cysteine is added to a target site at either N terminus or C terminus. Then the antigenic polypeptide will be easily bonded via a thiol bond to yield an immunogen. In a case where cysteine is already present in the amino acid sequence of a selected antigenic polypeptide, the polypeptide can also be attached by utilizing it. In a case where carbodiimidized KLH is used, it can be attached via a peptide bond formed with an antigenic polypeptide by dehydration condensation. In the present invention, a carrier protein is preferably attached to an antigenic polypeptide at the N terminus side.

A solution containing an immunogen prepared in this way is mixed with an adjuvant if desired, and then used to subcutaneously or intraperitoneally immunize an animal commonly used to raise antibody, such as rabbit, mouse, rat, guinea pig, sheep, goat and chicken, repeatedly every two to three weeks. Preferably, after immunization, blood is tentatively collected in an appropriate fashion to check if a titer (an antibody titer) is fully raised by using an immunological method such as ELISA and Western blotting. Blood is collected from an animal in which a sufficiently elevated titer is confirmed, and antiserum is obtained by separating its blood serum. In the case of chicken, a water-soluble fraction can be fractionated from the yolk collected from the hen egg to prepare a yolk extract, which also can be used similarly to antiserum.

In the present invention, the antiserum obtained can be used as it is without purification, but it is preferably purified for use by the following methods. The methods include, for example, a purification method using Protein A; a method using salt precipitation with ammonium sulfate; a method in which an immunoglobulin fraction is purified by ion exchange chromatography and the like; or a method of purification by affinity column chromatography using a column in which a specific polypeptide is immobilized. Among these, the purification method using Protein A and the method using affinity column chromatography are preferably used alone or in combination. For a polypeptide immobilized in a column for purification, depending on the amino acid sequence of an antigen polypeptide used, a polypeptide comprising the same sequence or a portion of the sequences may be selected.

Further, in a case where monoclonal antibody is raised, antibody-producing cells are collected from the spleen of an animal immunized as described above, and then, by a conventional method, fused with cultured cells such as myeloma cells from an allogeneic animal and the like to prepare hybridomas (Milstein et al., Nature, 256, 495 (1975)). After cultured, antibody titers may be appropriately determined by ELISA and the like to select a hybridoma which produces a monoclonal antibody that recognizes the target epitope, and also shows high antibody producibility. The target monoclonal antibody can be obtained from a culture supernatant of the hybridoma selected in this way.

The antibody obtained in this way specifically recognizes native CTP. This can be verified, for example, by collecting a sample from an appropriate animal species known to have CTP in perilymph and the like, and analyzing the reactivity with native CTP in the sample.

The antibody as used herein encompasses not only full length antibody but also a fragment of antibody. A fragment of antibody is preferably a functional fragment comprising an antigen binding region of antibody or a variable region thereof, including, for example, F(ab')$_2$, Fab', Fab and the like. F(ab')$_2$ and Fab', which are produced by treating immunoglobulin with a protease (for example, pepsin, papain, or the like), are antibody fragments generated by digestion at the sites before and after the disulfide bond present between the two H chains in the hinge region.

For example, when IgG1 is treated with papain, the disulfide bond present between the two H chains in the hinge region can be cleaved upstream the disulfide bond to yield two homologous antibody fragments in which a L chain fragment comprising VL (the L chain variable region) and CL (the L chain constant region) and a H chain fragment comprising VH (the H chain variable region) and CHγ1 (the γ1 region in the H chain constant region) are attached via a disulfide bond at the C terminal region. Each of the two homologous antibody fragments is called Fab'. Further, when IgG is treated with pepsin, IgG can be cleaved downstream the disulfide bond present between the two H chains in the hinge region to yield a slightly larger antibody fragment than a fragment in which two molecules of the above-mentioned Fab' were connected in the hinge region. This antibody fragment is called F(ab')$_2$.

Further, the antibody of the present invention can be used as an immobilized antibody supported on an insoluble support such as a solid phase support, or can be used as a labeled antibody labeled with a marker substance. All of these immobilized antibodies and the labeled antibodies are within the scope of the present invention.

An immobilized antibody means an antibody which is supported by an insoluble support via physical adsorption, chemical bonds, or the like. Such an immobilized antibody can be used to detect or quantify CTP contained in a sample. Insoluble supports which can be used to support antibody can include, for example, (1) plastics such as polystyrene resin, polycarbonate resin, silicon resin, or nylon resin; plates comprising a water insoluble substance represented by glass, latex, metallic compounds, magnetic materials and the like; articles having internal volume such as test tubes or tubes; beads; balls; filters; or membranes; and (2) insoluble supports used for affinity chromatography such as cellulose based supports, agarose based supports, polyacrylamide based supports, dextran based supports, polystyrene based supports, polyvinyl alcohol based supports, polyamino acid based supports, or porous silica based supports.

A labeled antibody means an antibody which is labeled with a labeling substance. Such a labeled antibody can be used to detect or quantify CTP contained in a sample. There is no particular limitation for labeling substances which can be used for the present invention as long as the presence of antibody becomes detectable by attaching a labeling substance to the antibody via physical association, chemical bonding or the like. Specific examples of labeling substances include enzymes, fluorescent substances, chemiluminescent substances, biotin, avidin or radioisotopes, and more specifically enzymes such as peroxidase, alkaline phosphatase, β-D-galactosidase, glucose oxidase, glucose-6-phosphate dehydrogenase, alcohol dehydrogenase, malate dehydrogenase, penicillinase, catalase, apo-glucose oxidase, urease, luciferase or acetylcholine esterase; fluorescent substances such as fluorescein isothiocyanate, phycobiliprotein, rare earth metal chelates, dansyl chloride or tetramethyl rhodamine isothiocyanate; radioisotopes such as $^3H$, $^{14}C$ and $^{125}I$ or $^{131}I$; biotin, avidin or chemiluminescent substances. Known methods such as the glutaraldehyde method, the maleimide method, the pyridyldisulfide method or the periodic acid method can be used as a method of attaching a labeling substance to an antibody.

In this context, radioisotopes and fluorescent substances can produce a detectable signal by themselves while enzymes, chemiluminescent substances, biotin and avidin will produce a detectable signal after further reacted with one or more other substances because they can not produce a detectable by itself. For example, in the case of enzymes, at least a substrate is required, and various substrates are used depending on the methods of measuring enzyme activity (the colorimetric method, the fluorescence method, the bioluminescence method or the chemiluminescence method). Further, in the case of biotin, it is usually reacted with at least avidin or enzyme modified avidin. Various chromogenic substances which depend on the above substrates are further used if desired.

2. A Method of Screening an Antibody Reacting with Native CTP

A method of screening an antibody reacting with native CTP of the present invention comprises a step of providing a native CTP captured by a first antibody reacting with native GIP and selecting a second antibody which recognizes the native CTP. The first antibody preferably recognizes an antigenic determinant included in the polypeptide represented by amino acid numbers 118-132 in the above-mentioned SEQ ID NO: 1, and reacts with native CTP.

That is, a new antibody reacting with native CTP can be obtained by using the antibody of the present invention. For example, in the ELISA method, a new antibody reacting with native CTP can be selected by screening a library of anti-CTP antibody as a second antibody using the antibody of the present invention as a first antibody. There is no particular limitation for antibody obtained with the screening method as long as it is an antibody reacting with native CTP, but it is preferably an antibody which recognizes a higher order structure or an antigenic determinant included in a region other than that of the polypeptide represented by amino acid numbers 118-132 of SEQ ID NO: 1.

3. A Method of Measuring a Protein Comprising the Polypeptide Represented by Amino Acid Numbers 118-132 of SEQ ID NO: 1

The measuring method of the present invention comprises the step of immunologically measuring a protein, preferably CTP, comprising the polypeptide represented by amino acid numbers 118-132 of SEQ ID NO: 1 using at least one antibody of the present invention. The measurements include both qualitative and quantitative measurements.

The method of measuring CTP of the present invention is suitably used for examining perilymph fistula.

In the present invention, perilymph fistula is a disease in which perilymph present in the inner ear tissue leaks from labyrinthine window (one or both of fenestra rotunda and fenestra ovalis) or fissura ante fenestram (bone fissure between the inner ear and the middle ear) into tympanum the middle ear) by unknown reasons to cause hearing disorder and balance disturbance. The disease can be detected by identifying perilymph leaked out to the middle ear. The method of detecting perilymph fistula of the present invention is a method comprising detecting the presence of CTP, which is present only in perilymph, in a body fluid which can be present in the middle ear of a suspected patient with this disease, the presence indicating a possibility that the patient suffers perilymph fistula. According to the present method, detection can be performed regardless of factors or mechanisms of the onset of perilymph fistula.

Suspected patients with this disease also include patients with sudden deafness, inner ear deafness, Meniere's disease, vestibular neuronitis, positional vertigo, inner ear vertigo and the like. Strictly speaking, they are diagnosises based symptoms. It has been pointed out for some time that perilymph fistula, which is diagnosis based the cause, is actually responsible for the above described diseases. Therefore, these diseases also can be examined by examining perilymph fistula with the method of the present invention.

As a sample which can be subjected to the method of detecting perilymph fistula of the present invention, a sample containing a body fluid which is present in the middle ear of a suspected patient with perilymph fistula is used. Body fluids which can be present in the human middle ear include, for example, perilymph, Cerebro-Spinal Fluid (hereinafter may be referred to as "CSF"), blood, saliva, middle ear mucus produced in middle ear mucous membrane and the like. For example, CSF is known to flow into the middle ear from the inner ear into which it has flown through a passway of the eighth cranial nerve in the internal auditory canal or the cochlear canaliculus as a result of surgery and the like. CSF is also known to flow into the middle ear due to injury, fracture, inner ear malformation and the like. Blood can be present in the middle ear as a result of bleeding due to injury, bleeding from middle ear mucous membrane and the like. Saliva is known to flow into the middle ear by reversed flow from the epipharynx through the auditory tube. Further, middle ear effusion for a patient with secretory otitis media, otorrhea (pus) for a patient with chronic otitis media and the like can be also present. These body fluids cannot be visually examined, but after collecting and analyzing a body fluid, the presence of CTP in a sample can be detected, thereby the presence of perilymph in the body fluid collected as the sample can be determined, the presence indicating possible perilymphatic fistula. Samples containing the above described body fluids include middle ear lavage fluid, nasal cavity swab fluid, upper throat swab fluid and the like.

Any methods of collecting a body fluid present in the middle ear can be used as long as they are less invasive for a patient, and can collect it with minimum contamination from blood, drugs and the like or with minimum contamination from other proteins. For example, a body fluid may be collected by microincision of tympanic membrane followed by inserting a syringe and the like to directly withdraw the body fluid, or by inserting a swab and the like to swab the body fluid. In a case where a body fluid to be collected is in a very small amount, a method is preferably used in which an appropriate amount of a suitable solution such as physiological saline is pored using a syringe and the like, and then the entire solution is recovered with a syringe and the like. In the present invention, a solution collected by this method is called a "middle ear lavage fluid." For a solution used in this method, selected is a solution which is physiologically acceptable in composition, pH, temperature and the like, and is less stressful to a patient. Further, since the middle ear is connected to the epipharynx and the oropharynx via the auditory tube, a body fluid from the middle ear which has reached the epipharynx and the oropharynx through the auditory tube can be collected. Specifically, for example, a body fluid in the epipharynx or the oropharynxcan can be collected by inserting a swab and the like through the oral cavity or the nasal cavity to swab it. These can be collected less-invasively and more simply than a middle ear lavage fluid collected by tympanotomy.

The method of measuring CTP of the present invention is also suitably used for diagnosis during craniocervical surgery.

For example, in chronic otitis media with cholesteatoma, external ear tumor, middle ear tumor, acoustic tumor and the like, perilymph fistula is known to be caused by osteoclasis. The present method can diagnose how deep the lesion is. That is, in a case where the lesion has damaged the bone and reached the inner ear, CTP will be detected from a body fluid present in the middle ear. In a case where the lesion is shallower, CTP will not be detected. Further, in tympanoplasty, stapes surgery and the like, a surgical intervention may be added to fenestra rotunda and fenestra ovalis. Whether surgical procedures have damaged these or not can be determined by the present measurement. Further, in cochlear implantation, the present measurement is useful to determine where an electrode of artificial cochlea to be inserted. In particular, it is highly useful for a case showing inner ear and middle ear malformation. In the case of examining these, a middle ear lavage fluid or a transudate from a lesion site or surgical site can be directly collected to be subjected to the examination.

There is no particular limitation for a sample to be used for the measurements as long as it contains CTP. Cell culture and the like may also be used. Further, a sample from a non human animal may be used to elucidate pathology in a laboratory animal. There is no particular limitation for laboratory animals, and they include, for example, guinea pig, rat, mouse, chinchilla and the like.

A body fluid collected in this way is preferably subjected to analysis immediately after collection, but may be stored under low temperature conditions such as 4 to −80° C., preferably −20 to −70° C. Upon storage, preservatives which suppress protein denaturation, antiseptic agents which prevent decomposition and the like may be added, if desired. Further, if desired, these samples may be subjected to pretreatment such as removal of hemocytes, tissue fragments and the like; concentration; purification; and the like before analysis. For specific procedures of these, publicly known and commonly used procedures for concentration and purification of proteins can be used.

A method of detecting the presence of CTP is an immunological method using the above described antibody which recognizes native CTP (hereinafter may be referred to as an "anti native CTP antibody"). For a method of immunologically detecting a protein, any publicly known and commonly used method can be used, for example, immunoassays in which labeled antibody is used, such as enzyme-linked immunoassay (ELISA), chemiluminescence immunoassay, immunofluorescence, radioimmunoassay and immunochromatography; or Western blotting in native conditions; the latex agglutination assay; immunonephelometry; and the like. Among these, the immunoassays in which labeled antibody is used are preferably used in view of simple operation and measurement accuracy. For intraoperative diagnosis, enzyme-linked immunoassay (ELISA), immunochromatography and the like are particularly preferred since rapid determination is required.

When the detection method of the present invention is performed by immunoassays in which labeled antibody is used such as enzyme-linked immunoassay (ELISA), chemiluminescence immunoassay, immunofluorescence, or radioimmunoassay, the sandwich method or the competition method also can be used. In the case of the sandwich method, at least one of the solid-phased antibody and the labeled antibody should be anti-native CTP antibody.

In a measurement by ELISA, an amount of perilymph leaked into the middle ear can be quantitatively measured by quantifying a luminescence signal. Since a CTP analog needs not be prepared, a sandwiched type measurement in which two different antibodies which recognize CTP at different epitopes is particularly prepared.

Solid phase supports used for the sandwich method may be any insoluble supports which can be used for supporting antibody, including, for example, 1) plastics such as polystyrene resin, polycarbonate resin, silicon resin, or nylon resin; plates comprising a water insoluble substance represented by glass, latex, metallic compounds, magnetic materials and the like; articles having internal volume such as test tubes or tubes; beads; balls; filters; or membranes, and (2) insoluble supports used for affinity chromatography such as cellulose based supports, agarose based supports, polyacrylamide based supports, dextran based supports, polystyrene based supports, polyvinyl alcohol based supports, polyamino acid based supports, or porous silica based supports.

Measurement operations can be performed in accordance with known methods (for example, Japan Society of Clinical Pathology Ed., "Immunoassay for laboratory test, technology and application," *Rinsyo Byori*, special edition, vol, 53, Rinsyo Byori Kankokai, 1983; Eiji Ishikawa et al. Ed., "Enzyme-linked immunoassay," 3rd edition, Igakusyoin, 1987; Tsunehiro Kitagawa et al. Ed., "Enzyme-linked immunoassay," *Proteins, nucleic acids and Enzymes*, Supp. No. 31, Kyoritsu Syuppan, 1987).

For example, a complex of solid phased antibody-antigen-labeled antibody is formed by reacting solid phased antibody with a sample, and simultaneously reacting labeled antibody, or reacting labeled antibody after wash. After washing and separating unbound labeled antibody, the amount of antigen in the sample can be measured from the amount of bound labeled antibody. Specifically, in the case of enzyme-linked immunoassay (ELISA), labeling enzyme is allowed to react with a substrate under its optimum conditions, and then the amount of the reaction product is measured by an optical method and the like. In the case of fluoroimmunoassay, fluorescence intensity from a fluorescent labeling substance is measured. In the case of radioimmunoassay, the amount of radiation from a radioactive labeling substance is measured. In the case of chemiluminescence immunoassay, the amount of luminescence from a luminescent reaction system is measured.

In a case where the detection method of the present invention, is performed by a measurement method in which the production of aggregated immune complex is measured by transmitted light and scattering light using an optical method, or is visually measured as in the latex agglutination reaction or immunonephelometry, phosphate buffer, glycine buffer, Tris buffer, or Good's buffer can be used as a solvent, and a reaction accelerator such as polyethylene glycol and non-specific reaction inhibitor further may be included.

In a case where an antibody supported on a solid phase support is used, particles comprising a material such as polystyrene, styrene-butadiene copolymer, (meta)acrylic ester based polymer, latex, gelatin, liposome, microcapsule, red blood cells, silica, alumina, carbon black, metallic compounds, metal, ceramics or magnetic materials can be used as a solid phase support.

For a method of preparing a supported material, known methods can be used such as physical adsorption, chemical bonding, or a combination thereof. Measurement operations can be performed by known methods. For example, when measuring by an optical method, a sample and an antibody, or a sample and an antibody supported on a solid phase support are reacted, and then transmitted light and scattering light are measured by the endpoint assay or the rate assay.

Further, in the case of visual measurements, a sample and an antibody supported on a solid phase support are reacted in a container such as a plate and a microtiter plate, and then the state of aggregation is visually determined. An instrument such as a microplate leader may be used for the measurements, instead of visual measurements.

When analysis is performed by the above described method using a body fluid present in patient's middle ear as a sample, the presence of CTP detected in the sample can indicate a possibility that this patient suffers perilymph fistula. The abundance of CTP in the body fluid can also be determined by quantification using a publicly known and commonly used protein quantification method.

4. A Kit for CTP Measurement

The kit for CTP measurement of the present invention comprises the antibody of the present invention. When the present reagent kit is used, the detection of perilymph fistula according to the present invention can be performed simply and rapidly at the time of need. The results can serve to discriminate it from other diseases and to determine treatment strategy and the like.

There is no particular limitation for forms of a reagent included in the kit. They may be a solid or a liquid (a solution, a suspension and the like). In the case of liquid, a reagent can be prepared by dissolving or suspending the above described antibody in an appropriate solvent (a buffer solution in which the antibody can be stably stored).

The kit of the present invention can be in any format as long as the detection method of the present invention can be performed. For example, in the case of a reagent kit in which CTP is checked by immunoassay using labeled antibody, the kit comprises at least an antibody reacting with native CTP as solid phased antibody on a support and/or labeled antibody. In addition, an enzyme substrate, a buffer solution such as a diluent and a washing solution, a positive control and the like may be included as optional elements. Accordingly, the reagent kit of the present invention comprises at least an antibody reacting with native CTP in a sample, and can be prepared by combining it with publicly known and commonly used reagents.

EXAMPLES

In the followings, the present invention will be described in more detail. However, the present invention shall not be limited by the following Examples within the gist of the present invention.

Example 1

Preparation of Anti CTP (*E. Coli*) Monoclonal Antibody

A polyhistidine tag was fused at the N terminal side of the amino acid sequence corresponding to amino acid numbers 32-132 in SEQ ID NO: 1 where the signal sequence of human CTP is removed, which was then expressed in *E. coli*. The expressed product was used as an immunogen to raise monoclonal antibody.

First, a nucleotide sequence prepared using the nucleotide sequence of human Cochlin as a reference was incorporated onto an *E. coli* expression vector, and *E. coli* was transformed with this vector. rCTP (recombinant CTP) encoded on the incorporated vector was induced by adding IPTG and expressed in the *E. coli*. The induced and expressed cells were harvested by centrifugation, and then lysed by sonication. After lysed, it was separated into a soluble fraction and an insoluble fraction by centrifugation. Since the expressed protein was obtained in a form of insoluble aggregates, the insoluble fraction was solubilized with urea, and affinity purification was performed with a nickel column. Mice were immunized with the resulting rCTP to obtain monoclonal antibody. Antibody screening was performed by detecting a reaction with rCTP by ELISA. A reaction between the resulting final monoclonal antibody and human CTP was checked by Western blotting.

(1) Expression of rCTP in *E. coli*

A primer for adding a translation initiation codon to the 5' end of ORF in which the signal sequence of CTP is removed (5'-<u>ATG</u> ATC ACA TGT TTT ACC AG-3': SEQ ID NO: 9), and a primer for adding a stop codon to the 3' end (5'-TAT TCA <u>TTA</u> CTC CTG TGT ACT ACT-3': SEQ ID NO: 10) were prepared to perform PCR amplification using IMAGE clone containing the COCH gene (IMAGE: 27789) (Kurabo industries Ltd, Osaka) as a template. In the sequences set forth in this section, a start codon and a stop codon were underlined.

The resulting PCT product was incorporated into an *E. coli* expression vector pCR T7/NT according to the package insert for pCR T7/NT-TOPO TA Expression Kit (Invitrogen), and then *E. coli* BL21 (DE3) pLysS cells included in the kit were transformed with the vector to obtain recombinant *E. coli* cells for expression of rCTP.

The resulting recombinant *E. coli* cells for expression of rCTP were inoculated into 1500 ml LB media supplemented with ampicillin, and cultured with shaking at 37° C. When the absorbance of the culture at 600 nm reached 0.5, IPTG was added to the culture to a final concentration of 0.1 mM, and further cultured with shaking at 37° C. for 3 hours.

(2) Purification of *E. coli* Expressed rCTP

The culture was centrifuged at 4° C. 3000 rpm for 30 minutes, and precipitated cells were collected, and then suspended in 10 ml lyse buffer (50 mM Tris-HCl pH 8.0, 50 mM NaCl, 1 mM EDTA). Cell suspension was sonicated on an ice to lyse the cells, and then centrifuged at 4° C., 3000 rpm for 30 minutes. The resulting precipitate was suspended in an inclusion body washing solution (0.5% Triton X-100, 1 mM EDTA), and then centrifuged 4° C., 3000 rpm for 30 minutes. This washing procedure was repeated three times. The washed precipitate was dissolved in 8 M urea to give an inclusion body solution.

The resulting inclusion body solution was loaded onto a nickel-NTA agarose equilibrated with a denaturing binding buffer solution (8 M urea, 500 mM NaCl, 20 mM sodium phosphate pH 7.8) to allow to react at room temperature for 1 hour. The resin after the reaction was recovered with a funnel having a glass filter, and washed with the denaturing binding buffer solution of 5-times volume of the resin, and then further washed with a denaturing washing buffer solution (8 M urea, 500 mM NaCl, 20 mM sodium phosphate pH 6.0) of 5-times volume of the resin. To the resin after washing, a denaturing elution buffer solution (8 M urea, 500 mM NaCl, 100 mM imidazol, 20 mM sodium phosphate pH 6.0) of 5-times volume of the resin was added, and then allowed to react for 1 hour. The reaction solution was recovered with a funnel having a glass filter to obtain rCTP expressed in *E. coli*.

(3) Preparation of a Monoclonal Antibody

The rCTP expressed in *E. coli* was cross-linked with KLH, and then used as an antigen. This antigen was administered to C57BL6 mice 3 times every two weeks in an amount of 50 μg each. Once increase in antibody titers was observed a week after the last immune sensitization by ELISA in which an *E. coli* expressed rCTP-immobilized plate was used, the spleen was removed and fused with myeloma for cell fusion (P3U1) by the PEG method. The resulting hybridomas were subjected to selection in HAT medium to obtain an antibody-producing hybridoma.

(4) Screening

*E. coli* expressed rCTP, which served as an immunogen, was solid-phased on a 96 well plate, and a reaction between this and a hybridoma culture supernatant was checked. Rabbit anti-mouse IgG/HRP (ZYMED) was used for detection. At the same time, a reaction with a β-actin solid-phased plate was also checked as a blank. Antibody which reacted with *E. coli* expression rCTP, but not with the blank was selected. Eventually only one positive strain was obtained (hereinafter may be referred to as "anti CTP (*E. coli*) antibody").

(5) Determining Reactivity with Human CTP by Western Blotting

Human perilymph used as a sample was obtained from a patient after collection and use thereof for research were fully explained, and consent was obtained.

The sample was mixed with 3× Loading buffer (1.50 mM Tris-HCl pH 6.8, 300 mM DTT, 6% SDS, 0.3% bromophenol blue, 30% glycerol), and heated at 100° C. for 5 minutes. The sample was applied on 15% polyacrylamide (PAGEL, ATTO Corporation), and electrophoresis was performed at 20 mA for 2 hours with a running buffer (25 mM Tris, 192 mM Glycine, 0.1% SDS), and then transferred on a PVDF film (Immobilon-PSQ, Millipore) by the semi dry method. Anti-CTP (*E. coli*) antibody as a primary antibody was allowed to react on the PVDF film after transfer, and then HRP-Rabbit anti-Mouse IgG (H+L) (ZYMED) was allowed to react as a secondary antibody. Then, a band at 16 kDa from CTP was checked using ECL Advance Western Blotting Detection Kit (GE health care) to determine if anti-CTP (E. coli) antibody recognized CTP in a human biological sample, Example 2

Preparation of Polyclonal Antibody

Anti-LCCL antibody, anti-LCCL1 antibody, anti-LCCL2 antibody, and anti-LCCL3 antibody used herein is described in Japanese Patent Laid-Open No. 2004-85552. Further, additional three different antibodies were raised using other polypeptides different from these as an antigen. A reaction between the resulting polyclonal antibody and human CTP was checked by Western blotting.

(1) Selection of the Amino Acid Sequence of an Antigen Polypeptide

For new antigen polypeptides, a polypeptide consisting of the amino acid sequence corresponding to amino acid numbers 34-49 in SEQ ID NO: 1 set forth in the Sequence Listing (antibody raised using this as antigen polypeptide may be referred to as "anti CTP-A antibody"), similarly a polypeptide consisting of the amino acid sequence corresponding to amino acid numbers 91-108 (antibody raised using this as antigen polypeptide may be referred to as "anti CTP-B antibody") and further a polypeptide consisting of the amino acid sequence corresponding to amino acid numbers 118-132 (antibody raised using this as antigen polypeptide may be referred to as "anti-CTP-C antibody") were selected for each.

Table 1 shows an immunized animal and an antigen polypeptide for each antibody, and FIG. 1 shows the position of each antigen polypeptide on the amino acid sequence set forth in SEQ ID NO: 1.

(2) Preparation of Polyclonal Antibody

A polypeptide consisting of the amino acid sequence selected in (1) was synthesized for each. Here, since cysteine was not contained in the amino acid sequences of antigen polypeptides for raising anti CTP-B antibody and anti CTP-C antibody, polypeptides in which cysteine was added to each sequence at the N terminus were synthesized. Bovine thyroglobulin as a carrier protein was added through the cysteine to give an immunogen.

Immunization was performed by administering 100 μg of the immunogen per rabbit every 1 to 2 weeks. After immunized 8 times, blood was withdrawn, and blood serum was separated to give antiserum. For each antiserum, a reaction against the antigenic polypeptide as an immunogen and E. coli expressed rCTP was checked by ELISA as in Example 1 (4), and then purification was performed using an antigen polypeptide-bound column prepared separately.

(3) Determining Reactivity with Human CTP by Western Blotting

Each polyclonal antibody was determined to recognize CTP in a human biological sample by using the same method as in Example 1 (5) except that anti-CTP-A antibody, anti-CTP-B antibody, or anti-CTP-C antibody was used as a primary antibody, and immunoglobulins/HRP [Goat Polyclonal Anti-Rabbit] (DAKO) was used as a secondary antibody.

Example 3

Determining Reactivity with Native CTP (Immunoprecipitation)

The fact that the antibodies prepared in Examples 1 and 2 were able to detect CTP by Western blotting showed that denatured CTP or CTP under denatured conditions can be detected. Accordingly, the following experiments were performed in order to find whether these antibodies also can detect native CTP.

TABLE 1

(an immunogen for each antibody)

| Antibody Name | Immunized animal | Antigen polypeptide |
|---|---|---|
| 1 Anti-LCCL antibody | Rabbit | Synthetic peptide (SEQ ID NO: 2) TRGLDIRKEKADVLC (36-50/15 mer) |
| 2 Anti-LCCL1 antibody | Rabbit | Synthetic peptide (SEQ ID NO: 3) GNIVYASVSSICGAAVHRGVI (63-83/21 mer) |
| 3 Anti-LCCL2 antibody | Rabbit | Synthetic peptide (SEQ ID NO: 4) LPGRENYSSVDANGIQS + C (95-111/18 mer) |
| 4 Anti-LCCL3 antibody | Rabbit | Synthetic peptide (SEQ ID NO: 5) LSRWSASFTVTKGK + C (114-127/15 mer) |
| 5 Anti-CTP-A antibody | Rabbit | Synthetic peptide (SEQ ID NO: 6) CFTRGLDIRKEKADVL (34-49/16 mer) |
| 6 Anti-CTP-B antibody | Rabbit | Synthetic peptide (SEQ ID NO: 7) C + RVYSLPGRENYSSVDANG (91-108/19 mer) |
| 7 Anti-CTP-C antibody | Rabbit | Synthetic peptide (SEQ ID NO: 8) C + SASFTVTKGKSSTQE (118-132/16 mer) |
| 8 Anti-CTP (E. coli) antibody | Mouse | A recombinant protein produced by expressing 32-132 in E. coli. |
| 9 Anti-CTP (Baculo) antibody | Mouse | A recombinant protein produced by expressing 1-132 in insect cells. |

Each antibody prepared in Examples 1 and 2 was bound to a Protein G immobilized support, and then allowed to react with swine perilymph or human perilymph. After reacted, a precipitate (an antigen-antibody complex bound to the Protein G immobilized support) and a supernatant (an unreacted antibody fraction) were collected, and Western blotting was performed after SDS-PAGE for each. By determining a fraction in which CTP was detected, whether each antibody recognized native CTP or not was determined.

Specifically, 30 µg of each antibody was allowed to react with 20 µg of Protein G on SEPHAROSE 4B (GE health care) equilibrated with PBS, and then unbound antibody was removed. To this antibody complex, 20 µl of swine perilymph or human perilymph diluted 10 times with PBS was added, and allowed to react overnight with shaking at 4° C. After reacted, centrifugation was performed at 4° C., 3000 rpm for 2 minutes to collect a supernatant and a precipitate for each.

Western blotting was performed by the method described in Example 1 (5) except that anti LCCL3 antibody was used as a primary antibody, and immunoglobulins/HRP [Goat Polyclonal Anti Rabbit] (DAKO) was used as a secondary antibody. The results are shown in Table 2. Those bound with native CTP are indicated as "YES," those not bound are indicated as "NO." The results showed that only anti-CTP-C antibody can recognize native CTP in perilymph.

TABLE 2

Reaction of each antibody with native CTP

| Antibody Name | Swine CTP | Human CTP |
| --- | --- | --- |
| Anti-LCCL antibody | NO | NO |
| Anti-LCCL1 antibody | — | NO |
| Ariti-LCCL2 antibody | — | NO |
| Anti-LCCL3 antibody | NO | — |
| Anti-CTP-A antibody | NO | NO |
| Anti-CTP-B antibody | NO | NO |
| Anti-CTP-C antibody | YES | YES |
| Anti-CTP (E. coli) antibody | — | NO |

Example 4

Preparation of a Monoclonal Antibody which Recognizes Native CTP

Production of anti-CTP (Baculo) monoclonal antibody was attempted in order to prepare a monoclonal antibody which recognizes native CTP.

The FLAG tag was fused to the C-terminal of the amino acid sequence corresponding to amino acid numbers 1-132 in SEQ ID NO: 1 which corresponds full length human CTP, and then expressed in silkworm. Monoclonal antibody was raised using this as an immunogen.

First, a nucleotide sequence prepared using the nucleotide sequence of human Cochlin as a reference was incorporated onto a transfer vector to establish a recombinant baculovirus strain. Silkworm pupa was infected with this to produce rCTP in silkworm. From the body fluid of the silkworm, affinity purification was performed with an anti-FLAG support. Mice were immunized with the resulting rCTP to obtain monoclonal antibody. Antibody screening was performed by detecting a reaction with rCTP by ELISA as well as a reaction with native human CTP captured by anti CTP-C antibody prepared in Example 3.

(1) Preparation of rCTP Expressed in Silkworm

A primer for adding a BglII recognition site to the 5 end of ORF of human CTP and a primer for adding a NheI recognition site to the 3' end were prepared, and PCR amplification was performed using a COCH gene-containing plasmid as a template. This PCR product was digested with BglII and NheI, and then inserted at the BglII and XbaI recognition sites in plasmid pM23 (Katakura Industries Co., Ltd.) to establish a. CTP recombinant baculovirus expression system. Silkworm pupa was infected with this CTP recombinant baculovirus. The body fluid of the silkworm after infection was absorbed on an anti-FLAG antibody column, and then the FLAG tag was cleaved with thrombin to obtain silkworm expressed rCTP.

(2) Antibody Preparation

Using silkworm expressed rCTP as an antigen, Balb/c mice were immunized at the foot pad with 50 µg of this antigen 4 times every other day. Then, collected lymph cells were fused with myeloma cells (P3U1) by the PEG method. The resulting hybridomas were subjected to selection in HAT medium to obtain antibody-producing hybridomas.

(3) Screening

A reaction of silkworm expressed rCTP as an immunogen and a hybridoma culture supernatant was checked by ELISA as in Example 1 (4). Goat anti-mouse IgG-POD F(ab')$_2$ (MBL) was used for detection.

The results are shown in Table 3. A reaction with silkworm expressed rCTP was observed for 11 hybridomas.

(4) Determining Reactivity with Human CTP

To an EIA plate (MAXISORP, Nunc), 5 µg/ml anti-CTP-C antibody was added at 100 µl/well and left to stand at 4° C. overnight. On the next day, 25% BLOCK ACE (Dainippon Sumitomo Pharma Co., Ltd.) was added at 300 µl/well, and blocked at 37° C. for 2 hours. After washing each well with a wash buffer (0.05% TWEEN-20, 20 mM PBS pH 7.4), human perilymph diluted 40 times with PBS was added at 100 µ/well, and allowed to react with shaking at room temperature for 1 hour. After washing each well, a hybridoma culture supernatant was added as a primary antibody at 100 µ/well, and allowed to react with shaking at room temperature for 2 hours. After washing each well, rabbit anti-mouse immunoglobulins/HRP (Dako) diluted 2000 times with 10% BLOCK ACE was added as a second antibody, and allowed to react with shaking at room temperature for 1 hour. After washing each well, SUREBLUE RESERVE TMB microwell substrate (KPL) was added at 100 µ/well, and allowed to react at room temperature for 15 minutes. Then a stop solution was added to quench the reaction. Absorbance at a wavelength of 450 nm was measured with a microplate reader.

Reactivities between the resulting 11 hybridomas and CTP in human perilymph were determined. The results are shown in Table 3. For 3C10, 7C1 and 7G1, a reaction with native CTP in human perilymph was detected. Further, difference in reaction intensity between silkworm expressed rCTP and CTP in human perilymph was observed depending on hybridomas.

TABLE 3

Reactivity of the resulting antibody with silkworm expressed rCTP and human CTP

| Clone No | Silkworm expressed rCTP (A450 nm) | Human perilymph (A450 nm) |
| --- | --- | --- |
| 3C1O | 1.773 | 4.073 |
| 7C1 | 1.262 | 2.011 |
| 7G1 | 1.384 | 0.218 |

TABLE 3-continued

Reactivity of the resulting antibody with silkworm expressed rCTP and human CTP

| Clone No | Silkworm expressed rCTP (A450 nm) | Human perilymph (A450 nm) |
|---|---|---|
| 2D10 | 4.157 | 0.088 |
| 1E8 | 4.173 | 0.081 |
| 2F6 | 2.641 | 0.079 |
| 4E12 | 4.122 | 0.064 |
| 7C9 | 2.410 | 0.053 |
| 4A10 | 3.057 | 0.041 |
| 8F10 | 2.546 | 0.034 |
| 1A11 | 2.114 | 0.024 |

Human perilymph or CTP in human perilymph could not be used in the conventional screening method in which an immunogen is solid-phased on a plate because they are difficult to be obtained in a large amount. Therefore, only an experiment could be performed in which rCTP used as an immunogen is immunized on the plate. Further, an immunogen might have been denatured since the immunogen is immobilized onto a plate. Thus, only a hybridoma having better reactivity with rCTP used as an immunogen could be selected in a case where only antibody which recognizes CTP under denatured conditions available. Therefore, it was difficult to prepare an antibody which recognizes native CTP. In contrast, screening by the sandwich ELISA method in which an antibody which recognizes native CTP was used as a solid phase antibody showed the ability of selecting an antibody which shows better reactivity with native CTP.

Example 5

Measurement of Native CTP in Human Perilymph by the Sandwich ELISA Method

Using anti CTP-C antibody as a solid phase antibody, CTP in human perilymph diluted in series using PBS was measured by the sandwich ELISA method with the 3C10 antibody prepared in Example 4. Measurements were performed as in Example 4 (4). The results are shown in FIG. 2. It was determined that native CTP in human perilymph can be measured in a concentration dependent fashion.

INDUSTRIAL APPLICABILITY

The antibody of the present invention is useful in the fields such as diagnosis, medical care and research.

The invention claimed is:

1. An antibody which recognizes an antigenic determinant included in the polypeptide consisting of amino acids 118-132 of SEQ ID NO: 1, wherein the antibody reacts with native Cochlin-tomoprotein (CTP) and wherein the antibody is obtained by using, as an immunogen, (i) a carrier protein attached to the polypeptide consisting of amino acids 118-132 of SEQ ID NO: 1 or (ii) a carrier protein attached to the polypeptide consisting of SEQ ID NO: 8.

2. A method of immunologically measuring CTP, comprising the steps of:
   collecting a sample suspected of containing CTP,
   reacting the sample with the antibody of claim 1 to allow the antibody to bind, and
   measuring the amount of bound antibody, thereby measuring CTP in the sample.

3. A kit for measuring CTP, comprising at least one antibody of claim 1.

4. The kit for measuring CTP of claim 3, which further comprises one or more reagents selected from the group consisting of an enzyme substrate, a buffer solution, a label, a solid support, and a positive control.

5. The antibody of claim 1, wherein the antibody is a monoclonal antibody or a polyclonal antibody.

6. The antibody of claim 5, wherein the antibody is a polyclonal antibody.

7. A method of assessing perilymph fistula in a subject, comprising the steps of:
   collecting a body fluid sample from a subject,
   reacting the sample with the antibody of claim 1 to allow the antibody to bind,
   measuring the amount of bound antibody,
   detecting the presence of CTP in the sample based on the measured amount of antibody, and
   diagnosing the presence of perilymph fistula in the subject when CTP is detected in the sample.

8. The method of assessing perilymph fistula of claim 7, wherein the detecting step is performed by a detection method selected from the group consisting of an enzyme-linked immunoassay (ELISA), a chemiluminescence immunoassay, an immunofluorescence assay, a radioimmunoassay, immunochromatography, Western blotting, a latex agglutination assay and immunonephelometry.

9. The method of assessing perilymph fistula of claim 7, wherein the antibody is labeled.

10. The method of assessing perilymph fistula of claim 9, wherein the labeled antibody is labeled with a labeling substance selected from the group consisting of enzymes, fluorescent substances, chemiluminescent substances, biotin, avidin, and radioisotopes.

11. The method of assessing perilymph fistula of claim 10, wherein the labeling substance is selected from the group consisting of peroxidase, alkaline phosphatase, β-D-galactosidase, glucose oxidase, glucose-6-phosphate dehydrogenase, alcohol dehydrogenase, malate dehydrogenase, penicillinase, catalase, apo-glucose oxidase, urease, luciferase, acetylcholine esterase, fluorescein isothiocyanate, phycobiliprotein, rare earth metal chelates, dansyl chloride, tetramethyl rhodamine isothiocyanate, biotin, avidin, $^{3}$H, $^{14}$C, $^{125}$I, and $^{131}$I.

12. An antibody which recognizes an antigenic determinant included in the polypeptide consisting of amino acids 118-132 of SEQ ID NO: 1, wherein the antibody reacts with native Cochlin-tomoprotein (CTP), and wherein the antibody is produced by the steps of:
   preparing, as an antigen, (i) a carrier protein attached to the polypeptide consisting of amino acids 118-132 of SEQ ID NO: 1 or (ii) a carrier protein attached to the polypeptide consisting of SEQ ID NO: 8,
   administering the antigen to an animal,
   obtaining antiserum containing the antibody from the animal, and
   purifying the antibody.

13. An antibody which recognizes an antigenic determinant included in the polypeptide consisting of amino acids 118-132 of SEQ ID NO: 1, wherein the antibody reacts with native Cochlin-tomoprotein (CTP), and wherein the antibody is produced by the steps of:
   preparing, as an antigen, (i) a carrier protein attached to the polypeptide consisting of amino acids 118-132 of SEQ ID NO: 1 or (ii) a carrier protein attached to the polypeptide consisting of SEQ ID NO: 8,
   administering the antigen to an animal,
   collecting antibody-producing cells from the spleen of the animal,
   fusing the antibody-producing cells with myeloma cells to prepare hybridomas,
   selecting a hybridoma which produces a monoclonal antibody that reacts with native CTP, and
   purifying the monoclonal antibody from the selected hybridoma.

* * * * *